United States Patent [19]

Uckun et al.

[11] Patent Number: 6,042,829
[45] Date of Patent: Mar. 28, 2000

[54] BIOTHERAPY OF CANCER BY TARGETING TP-3/P80

[75] Inventors: Fatih M. Uckun, White Bear Lake; Peter M. Anderson, St. Louis Park, both of Minn.

[73] Assignee: Regeants of the University of Minnesota, Minneapolis, Minn.

[21] Appl. No.: 08/909,976

[22] Filed: Aug. 12, 1997

Related U.S. Application Data

[62] Division of application No. 08/372,608, Jan. 13, 1995, Pat. No. 5,690,935.

[51] Int. Cl.[7] .................. A61K 39/395; A61K 39/44; C07K 16/30; C07K 14/415
[52] U.S. Cl. .................. 424/183.1; 424/134.1; 424/138.1; 424/143.1; 424/156.1; 530/388.85; 530/389.7; 530/391.7; 530/387.7
[58] Field of Search .................. 424/134.1, 138.1, 424/143.1, 156.1, 183.1; 530/388.85, 389.7, 391.7

[56] References Cited

U.S. PATENT DOCUMENTS

| 4,340,535 | 7/1982 | Voisin et al. |
| 4,350,626 | 9/1982 | Masuho et al. |
| 4,357,273 | 11/1982 | Masuho et al. |
| 4,359,457 | 11/1982 | Neville, Jr. et al. |
| 4,363,758 | 12/1982 | Masuho et al. |
| 4,368,149 | 1/1983 | Masuho et al. |
| 4,379,145 | 4/1983 | Masuho et al. |
| 4,414,148 | 11/1983 | Jansen et al. |
| 4,450,157 | 5/1984 | Masuho et al. |
| 4,590,071 | 5/1986 | Scannon et al. |
| 4,792,447 | 12/1988 | Uhr et al. |
| 4,806,494 | 2/1989 | Pastan et al. |
| 4,831,117 | 5/1989 | Uckun. |
| 4,888,415 | 12/1989 | Lambert et al. |
| 4,906,469 | 3/1990 | Jansen et al. |
| 4,916,213 | 4/1990 | Scannon et al. |
| 4,956,453 | 9/1990 | Bjorn et al. |
| 4,958,009 | 9/1990 | Bjorn et al. |
| 5,167,956 | 12/1992 | Neville, Jr. et al. |

FOREIGN PATENT DOCUMENTS

WO 93/23062  11/1993  WIPO.
WO 96/21467  7/1996  WIPO.

OTHER PUBLICATIONS

(1994) New York, American Cancer Society, pp. 1–28, Publication 94–375M—No. 5008.94 "American Cancer Society: Cancer Facts and Figures—1994".

Anderson, P.M. et al., (1995) *Anticancer Research*, 15(5A):1794–1795 "TP–3 Antibody—Pokeweed Antiviral Protein (TP–3–PAP) Conjugate Efficiently Kills Osteosarcoma".

Anderson, P.M. et al., (1995) *Cancer Research*, 55(6):1321–1327 "In Vitro and in Vivo Cytotoxicity of an Anti—Osteosarcoma Immunotoxin Containing Pokeweed Antiviral Protein".

Balis et al., (1993) *Principles and Practice of Pediatric Oncology*, 2nd ed., Pizzo et al., eds., J.B. Lippincott Company, Philadelphia, pp. 197–245 "General Principals of Chemotherapy".

Balis, F.M. et al., *Principles of Multimodal Therapy*, Chapter 10, pp. 197–245 "General Principles of Chemotheraphy".

Bologhesi et al., (1992) *Clin. Exp. Immunol.*, 89:341 "A comparison of anti–lymphocyte immunotoxins containing different ribosome—inactivating proteins and antibodies".

Bruland et al., (1993) *Frontiers of Osteosarcoma Research*, Novak et al., eds., Hogrefe and Huber Publishers, pp. 149–159 "Immunoscintigraphy and radioimmunotherapy: Useful approaches in the management of osteogenic sarcoma".

Bruland et al., (1986) *Int. J. Cancer*, 38:27 "New monoclonal antibodies specific for human sarcomas".

Bruland et al., (1986) *Br. J. Cancer*, 56(1):21–25 "Selective Localization of Radiolabeled Anti–Sarcoma Antibody".

Bruland et al., (1988) *Cancer Research*, 48:5302 "Expression and charateristics of a novel human osteosarcoma—associated cell surface antigen".

Byers, V.S. et al., (Oct. 1987) *Cancer Research*, 47:5042–5046.

Cheung et al., (1985) *J. Nat. Cancer Instit.*, 77:739.

Chin et al., (1986) *Hybridoma*, 5:339.

Dore et al., (1993) *Nucl. Acids Res.*, 21:4200–4205.

Elias et al., (1989) *Seminars in Oncology*, 16:305–311 "Adjuvant chemotherapy for soft tissue sarcoma: an approach in search of an effective regimen".

Embelton et al., (1981) *Br. J. Cancer*, 43:582.

Embleton et al., (Nov. 1986) *Cancer Res.*, 46:5524–5528.

Erice et al., *Blood*.

Fodstad et al., (1986) *Int. J. Cancer*, 38:33 "Characteristics of a cell line established from a patient with multiple osteosarcoma, appearing 13 years after treatment for bilateral retinoblastoma".

Folkman et al., (1991) *Biological Therapy of Cancer: Alternative Strategies for Biologic Therapy*, DeVita et al., eds., J.B. Lippincott Company, Chapter 30, pp. 743–753 "Anti-angiogensis".

Frei et al., (1993) *Frontiers of Osteosarcoma Research*, Novak et al., eds., Hogrefe and Huber, pp. 5–13 "Osteogenic Sarcoma: The Development of Curative Treatment".

(List continued on next page.)

*Primary Examiner*—Paula K. Hutzell
*Assistant Examiner*—Geetha P. Bansal
*Attorney, Agent, or Firm*—Merchant & Gould

[57] ABSTRACT

Cytotoxic biotherapeutic agents effective for treating certain types of cancer in humans are provided which comprise the TP-3 murine monoclonal antibody chemically conjugated to pokeweed antiviral protein (PAP). The invention further provides a method which utilizes the disclosed cytotoxic biotherapeutic agents to systemically treat cancer patients. With slight modifications the method of the present invention should be generally applicable to preparation and use of other cytotoxic biotherapeutic agents using chemical or recombinant derivatives of the TP-3 or TP-1 antibodies or PAP toxin. The invention is applicable to cancer patients who express the p80 antigen recognized by the TP-1/TP-3 antibodies either on the surface of their tumor cells or on the tumor blood vessels.

16 Claims, 6 Drawing Sheets

OTHER PUBLICATIONS

Gellego, J. et al., (1985) *Database Embase*, 21(11):511–521.
Ghetti et al., (Aug. 1994), *Blood*, 84:702–707.
Gottstein et al., (1994) *Annals of Oncology*, 5:S97.
Guther et al., (Feb. 1993), *Leukemia*, 7:298–309.
Haines, D.M. et al., (1989) *Anticancer Research*, 9:903–908.
Hertler et al., (1989) *J. Clin Oncol.*, 7:1932.
Hosi et al., (1982) *Cancer Research*, 42:654.
Houston et al., (1987) *Immunological Antibody Conjugates in Radioimaging and Therapy of Cancer*, C.W. Vogel, ed., New York, Oxford University Press, p. 71 "Immunotoxins made with Toxins and Hemitoxins other than Ricin".
Irvin et al., (1992) *Pharmac. Ther.*, 55:279 "Pokeweed antiviral protein: ribosome inactivation and therapeutic applications".
Irvin, (1983) *Pharmacol. Ther.*, 21:371.
Jansen et al., (1992) *Leukemia*, 7:290.
Kersey et al., (Jun. 19–21, 1992), Third International Symposium on Immunotoxins, Orlando, FL, p. 95.
McClay E. F., (1989) *Seminars in Oncology*, 16:264–272 "Epidemiology of Bone and Soft Tissue Sarcomas".
McClay et al., (1989) *Seminars in Oncology*, 16:328–332 "Immunotherapeutic Approaches to the Treatment of Bone and Soft Tissue Sarcomas".
Mendelsohn, (1992) *J. Natl Cancer Inst.*, 13:125–131.
Meyers et al., (1993) *J. of Clinical Oncology*, 11:4490453 "Osteogenic sarcoma with clinically detectable metastasis at initial presentation".
Milstein, (1980) *Sci. Am.*, 243:66.
Myers et al., (1988) *Transplantation*, 46:240.
Myers et al., (1991) *J. Immun. Methods*, 136:221–238.
Myers et al., (1995) *PNAS USA*, 92:9575–9579.
Canevari et al., (1994) *Annals. of Oncology*, 5:698–701.
Naramura, (1993) *Cancer Immunol. Immunother.*, 37:343–349.
Pastan et al., (1986) *Cell*, 47:641 "Immunotoxins".
Perentesis et al., (1988) *PNAS USA*, 85:8386.
Perentesis et al., (1991/1992) *Biofactors*, 3:178–184.
Perentesis et al., (Mar. 1, 1993) Abstract CA–53586.
Perentesis et al., (Sep. 1, 1987) Abstract AI–00793.
Ramakrishnan, S. et al., (Apr. 1984) *Cancer Research*, 44(4):1398–1404.
Ramsay et al., (Jun. 1992) 3rd Int'l. Symposium on Immunotoxins, ORlando, FL.
Raymond et al., (1987) *Seminars in Diagnostic Pathology*, 4:212–236 "Osteosarcoma chemotherapy effect: A prognostic factor".
Rivera et al., (Oct. 28, 1993) *The New England J. of Med.*, 329:1289–1295.
Roth, J.A. et al., (1978), *Database Embase*, Elsevier Science Publishers, Abstract & Cancer, 41(3):814–819.
Thomas, (1992) *Drugs of Today*, 28:311–331.
Tsai et al., (1990) *Cancer Research*, 50:152.
Tsang et al., (1986) *J. Nat. Cancer Inst.*, 77:1175.
Uckun et al., (1985), *J. Immunol*, 134:2010.
Uckun et al., (1986) *J. Exp. Med.*, 163:347 "Use of a novel colony assay to evaluate the cytotoxicity of an immunotoxin containing pokeweed antiviral protein against blast progenitor cells freshly obtained from patients with common B–lineage acute lymphoblastic lsukemia".
Uckun et al., (1988) *Blood*, 7(13).
Uckun et al., (1989) *In: Human Tumor Antigens and Specific Tumor Therapy*, R. Metzger & M. Mitchell, eds,. Alan R. Liss, Inc., NY, NY, pp. 231–241.
Uckun et al., (1989) *Int. J. Radiat. Biol.*, 56:611–615.
Uckun et al., (1990) *Blood*, 76:2449.
Uckun et al., (Feb. 1993) *Leukemia*, 7:341.
Uckun et al., (Jun. 19–21, 1992), Third International Symposium on Immunotoxins, Orland, FL, p.131.
Uckun et al., (May 1, 1992) *Blood*, 79:2201.
Uckun et al., (May 1992), *Blood*, 79:2649–2661.
Uckun et al., *In: Membrane—Mediatal Cytotoxicity*, pp. 243–256.
Uckun, (1988) *Antibody Immunoconjugates and Radiopharmaceutics*, 1:247.
Uckun, (Nov. 9, 1993) *Brit. J. Haematol.*, 85:435.
Vitetta et al., (1991) *Biologic Therapy of Cancer*, DeVita et al., eds., J.B. Lippincott Company, pp. 482–495 "Immunotoxins".
Vitetta et al., (2987) *Science*, 225:1098–1104.
Wada et al., (1988) *Cancer Research*, 48:2273.
Ward et al., (1994) *Journal of Clinical Oncology*, 12:1849–1858 "Pulmonary Metastases of Stage IIB Extremity Osteosarcoma and Subsequent Pulmonary Metastases".
Wingo et al., (Jan./Feb. 1995) *A Cancer J. for Clinicians*, 45:8–30.
Winker et al., (1988) *J. of Clinical Oncology*, 6:329–337 "Neoadjuvant Chemotherapy of Osteosarcoma: Results of a Randomized Cooperative Triel (Coss–82) with Salvage Chemotherapy Based on Histologic Tumor Response".

BIOTHERAPY OF CANCER BY TARGETING TP-3/P80

This is a Divisional of application Ser. No. 08/372,608, filed Jan. 13, 1995 (now U.S. Pat. No. 5,690,935), which is hereby incorporated by reference.

BACKGROUND OF THE INVENTION

Osteosarcoma

Sarcomas, malignancies of mesodermal origin, develop mainly in bone and soft tissues. McClay et al., "Immunotherapeutic Approaches to the Treatment of Bone and Soft Tissue Sarcomas", *Seminars in Oncology* 16, 328 (1989). Together, these tissues constitute greater than 60% of the adult body weight. McClay, "Epidemiology of Bone and Soft Tissue Sarcomas", *Seminars in Oncology* 16, 264 (1989). Despite this, the malignant degeneration of this tissue is rare. It is estimated that there were 2,000 new cases of bone sarcomas and 6,000 new cases of soft tissue sarcomas in 1994. *American Cancer Society: Cancer Facts and Figures*—1994, New York, American Cancer Society, 1994, p. 6. Together they constitute approximately 0.8% of all cancers diagnosed in the United States.

Although these sarcomas are not common, a significant number of patients who develop these tumors will die with metastatic disease. In fact, before 1972, the mortality for patients presenting with metastatic osteogenic sarcoma was 100%. Frei et al., "Osteogenic Sarcoma: The Development of Curative Treatment", In: *Frontiers of Osteosarcoma Research* Novak et al., eds., Hogrefe and Huber, pp. 5–13 (1993). For patients without metastatic disease, the majority required amputation to control the primary tumor and in spite of this, 80% of patients relapsed and died largely due to lung metastases. Bruland et al., "Immunoscintigraphy and Radioimmunotherapy: Useful Approaches in the Management of Osteogenic Sarcoma?", In: *Frontiers of Osteosarcoma Research*, Novak et al., eds., Hogrefe and Huber, pp. 149–159 (1993).

Relapse-free survival and overall survival have since been substantially increased by adjuvant chemotherapy. However, in spite of considerable progress in the treatment of patients with osteogenic sarcomas during the past 20 years, using regimens that include high-dose methotrexate, doxorubicin, and alkylating agents such as cyclophosphamide, ifosfamide and cisplatin, 40% of these patients still succumb to the disease. Ward et al., "Pulmonary Metastases of Stage IIB Extremity Osteosarcoma and Subsequent Pulmonary Metastases", *Journal of Clinical Oncology*, 12, 1849 (1994). Osteosarcoma patients relapsing after first-line treatment because of regrowth chemotherapy-resistant tumor cells seem to gain only marginal benefit from aggressive second-line chemotherapy.

Thus, patients with osteosarcoma require more effective detection and elimination of chemotherapy resistant disease. As mentioned above, adjuvant chemotherapy is a standard treatment approach for many sarcomas including Ewing's sarcoma, rhabdomyosarcoma, and osteosarcoma. Balis et al., "General Principals of Chemotherapy", In: *Principles and Practice of Pediatric Oncology*, 2nd ed., Pizzo et al. eds., J. B. Lippincott Company, Philadelphia, pp. 197–245 (1993). It has been more difficult, however, to demonstrate significant benefit of chemotherapy in adult soft tissue sarcomas and osteosarcoma with metastatic disease at diagnosis or after the development of lung metastases. Elias et al., "Adjuvant chemotherapy for soft tissue sarcoma: an approach in search of an effective regimen", *Seminars in Oncology*, 16, 305 (1989); Meyers et al., "Osteogenic sarcoma with clinically detectable metastasis at initial presentation", *J. of Clinical Oncology* 11, 449 (1993).

Drug targeting is a potentially attractive new approach to killing malignant cells, which leaves normal tissues unharmed. A breakthrough in drug targeting was the advent of hybridoma technology, making monoclonal antibodies (MoAb) available for clinical applications. To construct reagents with selectivity for certain populations of tumor cells, MoAbs or other cell targeting proteins are linked to cytotoxic agents to form molecules referred to as biotherapeutics which potentially combine the selectivity of the carrier moiety (e.g., MoAb) with the potency of the cytotoxic moiety. The choice of carrier moiety can be based on the surface antigen profile of a given malignant cell determined by reaction with an enzyme or fluorescently labelled antibody.

For the past decade, biotherapeutics have been under investigation for the treatment of various cancers, and more recently, for the treatment of immunological disorders such as rheumatoid arthritis and acquired immune deficiency syndrome (AIDS). Although these agents have shown some potential to provide safe and effective therapy for certain human pathologies, many difficulties remain. Ideally, consistently locatable and reliable markers on target cells would permit the binding portion of biotherapeutics to completely avoid binding to non-target tissue. In reality, cross-reactivity with antigens expressed by vital organs often gives rise to unacceptable complications in in vivo applications. There is also the potential that a patient will demonstrate immune responses to the separate components of the biotherapeutic agent, especially if they are not natural human proteins, even though the patient may already be immunosuppressed by the course of their disease. Moreover, the cytotoxicity obtained in in vitro studies may be limited in clinical application due to a lack of potency in doses that can be tolerated by the patient. Furthermore, solid tumors are difficult to penetrate thoroughly, resulting in the possibility of residual disease which can cause relapse. Finally, the rarity and heterogeneity of sarcomas has made the development of biotherapeutic agents against these cancers difficult. McClay, E. F., "Epidemiology of bone and soft tissue sarcomas", *Seminars in Oncology* 16, 264 (1989); McClay et al., "Immunotherapeutic approaches to the treatment of bone and soft tissue sarcomas", *Seminars in Oncology,* 16, 328, (1989).

Hence, there is a strong need to develop new treatment strategies for patients afflicted with sarcomas. Since the degree of necrosis of osteosarcoma in the neoadjuvant chemotherapy setting has been shown to be a highly significant predictor of disease free survival, a need further exists to increase the proportion of osteosarcoma patients with favorable initial responses to neoadjuvant chemotherapy as well as to develop novel treatments for patients with poor responses or metastatic disease. Raymond et al., "Osteosarcoma chemotherapy effect: A prognosite factor", *Seminars in Diagnostic Pathology* 4, 212 (1987); Winkler et al., "Neoadjuvant Chemotherapy of Osteosarcoma: Results of a Randomized Cooperative Triel (COSS-82) with Salvage Chemotherapy Based on Histologic Tumor Response", *J. of Clinical Oncology* 6, 329, (1988).

SUMMARY OF THE INVENTION

The present invention provides cytotoxic biotherapeutic agents which comprise a toxin, preferably pokeweed antiviral protein (PAP), linked to a carrier, preferably an antibody or antibody fragment which binds to the p80 cell surface receptor. The p80 antigen is associated with the tumor cells as well as tumor blood vessels of cancers such as osteosarcoma or soft tissue sarcoma. The toxin portion of the biotherapeutic agent acts to inhibit the division of, or to kill the target tumor cell without a significant non-specific toxicity (i.e., innocent bystander effect) on surrounding normal tissues that do not express the cell surface receptor for which the antibody is specific. Further, the biotherapeutic agent may kill the target tumor not only directly by exhibiting cytotoxicity to the individual tumor cells but also indirectly by killing the blood vessels responsible for carrying oxygen and nutrients to the tumor. Rapid necrosis of xenografted human osteosarcoma was observed in a SCID mouse model. Most importantly, survivial of SCID mice xenografted with human osteosarcoma was markedly improved upon treatment with TP-3-PAP, due to this particular biotherapeutic agent's prevention of tumor progression. The cytotoxicity exhibited by the bioactive agents of the present invention was unexpectedly potent, since neither unconjugated PAP nor unconjugated TP-3 inhibited tumor cell growth, even at much higher concentrations.

The present invention is based, in part, upon the finding that the p80 antigen recognized by TP-1 and TP-3 monoclonal antibodies is apparently unique to sarcomas and furthermore, that the distribution of the TP-1/TP-3 antigen is very limited on normal tissues. Thus, a preferred embodiment of the invention comprises a cytotoxic amount of a PAP molecule linked to a carrier such as a monoclonal antibody or antibody fragment which binds specifically to a receptor on a sarcoma cell. Thus, preferred carriers are TP-1 and TP-3 as well as Fab or $Fab_2$, which are active fragments of TP-3, and single chain FV (scFV) of TP-1 or TP-3, a recombinant antibody which recognizes the target antigen. Most preferably, the carrier used will be TP-3 or its active fragments Fab, $Fab_2$ or scFV. The bioactive agent resulting from the conjugation of PAP and the preferred carrier can be designated TP-3-PAP. As used herein, the term "carrier" includes antibodies, antibody fragments and subunits thereof which are at least equivalent in their binding specificity. As used herein with respect to PAP, a "cytotoxic amount" means that at least one, i.e., 1–3 molecules of PAP are linked to each antibody molecule.

Mouse hybridoma cells TP1 and TP3 were deposited with the American Type Culture Collection (ATCC) on Apr. 11, 1997 and received ATCC designations HB-12339 and HB-12340, respectively. These cultures were tested and found viable on May 1, 1997.

The present invention also provides a therapeutic method for the treatment of target cancers. The method comprises parenterally administering to a patient who is afflicted with a target cancer an effective amount of a pharmaceutical composition comprising a biotherapeutic agent consisting of monoclonal antibody TP-3 covalently linked to an effective cytotoxic amount of PAP, in combination with a pharmaceutically acceptable carrier. As used herein, the phrase "target cancer" refers to diseases associated with the proliferation of mammalian cells expressing the antigen recognized by TP-1 and TP-3, i.e., the p80 antigen. The p80 antigen may be expressed either on the tumor blood vessels or the tumor cells themselves of the target cancer. Such target cancers include, but are not limited to, other human sarcomas including osteosarcoma, hemangiopericytoma, chondrosarcoma, malignant fibrous histiocytoma (MFH), Kaposi's sarcoma, fibrosarcoma and synovial cell sarcoma. As used herein, the term "PAP" refers to any cytotoxic pokeweed antiviral protein, or derivative thereof, including subtypes PAP-II and PAP-S. The high cytotoxicity action of this immunotoxin was unexpected since neither PAP nor TP-3 alone was found to be cytotoxic at equivalent, or greater, concentration. Furthermore, TP-3-PAP was found to be much more potent than PAP immunoconjugates directed against leukemia-associated antigens (e.g., B43-PAP).

Furthermore, since p80 antigen is present on budding capillaries of a wide variety of cancers and osteosarcoma, a p80 directed biotherapeutic agent such as TP-3-PAP, can inhibit the growth of sarcomas not only by selectively destroying cancer cells but also the vascular endothelium of the tumor. As any tumor greater than one millimeter in size requires neovasculature to grow in size, the destruction in such neovasculature results in the ultimate death of the tumor. Folkman et al., In: *Biologic Therapy of Cancer*, DeVita et al., eds., J. B. Lippincott Company, pp. 743–753 (1991). Furthermore, such destruction may also facilitate the entry of antineoplastic agents into the solid tissue of the tumor. Put another way, in addition to the destruction of the tumor vasculature, the TP-3-PAP biotherapeutic agent may further aid the entry of antineoplastic agents by providing damage sites or "windows" in the tumor vasculature through which the antineoplastic agents may enter the tumor.

Thus, a further embodiment of the present invention comprises the administration of a biotherapeutic agent followed by administration of an effective amount of one or more conventional antineoplastic agents. Preferably, the antineoplastic agents employed are doxorubicin, methotrexate, etoposide, and alkylating agents such as the oxazaphosphorines (cyclophosphamide and ifosfamide) and platinum compounds such as cisplatin and carboplatin.

BRIEF DESCRIPTION OF THE FIGURES

FIGS. 1A, 1B and 1C depict the purification and characterization of TP-3-PAP. Specifically.

FIGS. 2A and 2B illustrate the proliferation of human OHS osteosarcoma cells after treatment with TP-3 MoAb, PAP, and TP-3-PAP immunotoxin as determined by a $^3H$ thymidine incorporation assay. Specifically, FIG. 2A shows that TP-3-PAP, but not TP-3 MoAb alone inhibited growth of OHS cells, while

FIGS. 3A and 3B depict the effect of TP-3-PAP on TP-3 negative cell lines. Specifically.

DETAILED DESCRIPTION OF THE INVENTION

Immunotoxins

Immunotoxins (antibody-toxin conjugates) are a relatively new class of biotherapeutic agents that are prepared by covalently linking cell type-specific polyclonal or monoclonal antibodies to one of a variety of catalytic toxins either directly, as via a covalent bond, or via a linking agent. Pastan et al., "Immunotoxins", *Cell*, 47, 641 (1986). In the case of sarcoma, as discussed below, immunotoxin technology provides a potent means to achieve effective therapeutic use of the TP-3 and TP-1 MoAb.

1. Monoclonal Antibodies

Monoclonal antibodies (MoAbs) are produced by the fusion of spleen lymphocytes with malignant cells (myelomas) of bone marrow primary tumors. Milstein, *Sci. Am.* 243 66 (1980). The procedure yields a hybrid cell line, arising from a single fused cell hybrid, or clone, which possesses characteristics of both the lymphocytes and myeloma cell lines. Like the lymphocytes (taken from animals primed with sheep red blood cells as antigens), the fused hybrids or hybridomas secrete antibodies (immunoglobulins) reactive with the antigen. Moreover, like the myeloma cell lines, the hybrid cell lines are immortal. Specifically, whereas antisera derived from vaccinated animals are variable mixtures of antibodies which cannot be identically reproduced, the single-type of immunoglobulin secreted by a hybridoma is specific to one and only one determinant on the antigen, a complex molecule having a multiplicity of antigenic molecular substructures, or determinants (epitopes). Hence, monoclonal antibodies raised against a single antigen may be distinct from each other depending on the determinant that induced their formation. However, all of the antibodies produced by a given clone are identical. Furthermore, hybridoma cell lines can be reproduced indefinitely, are easily propagated in vitro and in vivo, and yield monoclonal antibodies in extremely high concentration.

a. TP-1/TP-3

Because bone and soft tissue sarcomas in general are rare, the individual subtypes are even less common. Although this has hampered the development of tumor specific MoAbs, some progress has been made. Additionally, a number of antibodies have been generated that seem to recognize antigens shared by several types of sarcomas. The majority of MoAbs against sarcoma antigens are in the developmental stage. Relatively few are ready for clinical trials.

Monoclonal antibodies TP-1 and TP-3 have been shown to react with different epitopes of an 80 kd antigen on human and canine osteosarcoma which is referred to as the p80 antigen. Bruland et al., "New monoclonal antibodies specific for human sarcomas", *Int. J. Cancer*, 38, 27 (1986). Specifically, TP-3 is an $IgG_{2b}$ monoclonal antibody which recognizes mesenchymal tumors including osteosarcomas as well as the budding capillaries of a wide variety of tumors. Bruland et al., *Cancer Research* 48, 5302 (1988). TP-1 and TP-3 also bind a variety of other human sarcomas including hemangiopericytoma, chondrosarcoma, malignant fibrous histiocytoma (MFH), and synovial cell sarcoma. Bruland et al., "Expression and characteristics of a novel human osteosarcoma-associated cell surface antigen", *Cancer Research*, 48, 5302 (1988).

The distribution of the TP-1/TP-3 antigen on normal tissues is very limited. This limited tissue distribution that makes the TP-3 antigen an attractive choice for immunotoxin therapy. The current state of knowledge of distribution of the TP-1/TP-3 antigen on normal tissues and mesenchymal tumors has been recently summarized by Bruland and Phil. "Immunoscintigraphy and radioimmunotherapy: Useful approaches in the management of osteogenic sarcoma" In: *Frontiers of Osteosarcoma Research* J. F. Novak and J. H. McMaster (eds.), Hogrefe and Huber Publishers, pp. 149–159, (1993). Negative tissues included fibroblasts, peripheral blood cells, cells in the marrow, fetal skin fibroblasts, fetal lung fibroblasts, amniocytes, fibrous connective tissue, skeletal muscle, cartilage, synovia, peripheral nerve, tonsil, spleen, liver, colon, and lung. Only newly active bone callus, placental endothelial cells, proximal tubule of kidney (weak binding), and occasional cells in the adrenal medulla were positive for TP-1 and TP-3 binding. Bruland et al., *Cancer Research* 48, 5302 (1988).

b. Other Carriers

In addition to TP-1 and TP-3, several other antibodies have been found to be reactive with human osteosarcoma and thus, are suitable for use in the present invention as a PAP conjugate. See Table 1, below. Although in vitro testing has been conducted with a variety of these antibodies, this testing has not been carried out with the antibodies conjugated to PAP. Furthermore, no in vivo testing of an immunotoxin utilizing these antibodies against osteosarcome has been reported.

TABLE 1

Monoclonal Antibodies Reactive with Human Osteosarcoma

| MAB name | MW Antigen | Tumor Reactivity Profile | Reference |
|---|---|---|---|
| TP-1 and TP-3 | 80,000 | osteosarcomas | 1 |
|  |  | hemangiopericytomas | 1 |
|  |  | budding tumor capillaries | 2 |
| Ost 6,7 | 86,000 | osteosarcomas | 3 |
|  |  | alkaline phosphatase |  |
| 791T/36 | 72,000 | osteosarcomas | 4 |
|  |  | colon carcinoma, stroma |  |
| TM-2 | 26,000 | osteosarcoma | 5 |
| OS-1 | unknown | osteosarcoma | 6 |
| 3F8 |  | osteosarcoma | 7 |
|  |  | melanoma, neuroblastoma |  |
| OSA-1, OS-2 | 92,000 | osteosarcoma | 8 |
| 2D3, 2H10 | 75,000 | osteosarcoma | 9 |

1. Bruland et al., Int. J. Cancer, 38, 27 (1986)
2. Bruland et al., Cancer Research, 48, 5302 (1988).
3. Hosi et al., Cancer Research, 42, 654 (1982).
4. Embelton et al., Br. J. Cancer, 43, 582 (1981).
5. Tsai et al., Cancer Research, 50, 152 (1990).
6. Chin et al., Hybridoma, 5, 339 (1986).
7. Cheung et al., J. Nat. Cancer Instit., 77, 739 (1985).
8. Tsang et al., J. Nat. Cancer Inst, 77, 1175 (1986).
9. Wada et al., Cancer Research, 48, 2273 (1988).

2. Toxins

The variety of toxins that have been employed in immunotoxins by various investigators can be broadly categorized into two groups. The first group consists of intact toxins, such as ricin. Ricin consists of two subunits, the A chain which is capable of inactivating as many as 1,500 ribosomes per minute and the B chain which recognizes non-reducing terminal galactose residues on cell surfaces and facilitates A chain entry. Although intact ricin immunotoxins are highly effective destroyers for their target cells, they cannot be applied for in vivo treatment of leukemia because of the nonselectability of their B chain moiety.

The second group of toxins are referred to as hemitoxins. Hemitoxins are single-chain ribosome inactivating proteins that act catalytically on eukaryotic ribosomes and inactivate the 60-S subunit, resulting in an irreversible shut-down of cellular protein synthesis at the level of peptide elongation. Such polypeptide toxins have been isolated from pokeweed (*Phytolacca americana*), bitter gourd (*Momordica charantia*), wheat (*Tritium vulgaris*), soapwort (*Saponaria officinalis*), *Gelonium multiflorum*, and several other plants. Since these ribosome inactivating proteins, unlike intact ricin, do not have a B chain subunit with nonselective cell binding capacity, they cannot easily cross the cellular membrane. Therefore, hemitoxins are practically devoid of toxicity to intact eukaryotic cells.

a. PAP

There are three subtypes of pokeweed antiviral protein (PAP) the expression of which are dependent upon the season. PAP is found in spring leaves, PAP II is found in late summer leaves, and PAP-S is found in the seeds. Irvin, *Pharmacol. Ther.* 21, 371 (1983). Small differences exist in their sizes (all are approximately 29,000 MW) and there are only small differences, if any, between their ability to inhibit ribosomes catalytically. Houston et al., "Immunotoxins made with Toxins and Hemitoxins other than Ricin", in *Immunological Antibody Conjugates in Radioimaging and Therapy of Cancer* C. W. Vogel, ed., New York, Oxford University Press, P. 71 (1987).

PAP is a member of the hemitoxin group of toxins and thus inactivates ribosomes by the specific removal of a single adenine from the conserved loop sequence found near the 3' terminus of all larger rRNAs. Irvin et al., *Pharmacology and Therapeutics*, 55, 279, (1992). This specific depurination greatly reduces the capability of elongation factors to interact with ribosomes and results in an irreversible shut-down of protein synthesis. Irvin et al., cited supra. Furthermore, PAP is one of the most active ribosomal inactivating proteins. In a comparison of cytotoxicity of anti-mouse IgG immunotoxins gelonin, ricin A chain, momordin, dianthin 32, saporin, and PAP, the PAP constructs were among the most potent immunotoxins tested. Bolognesi et al., "A comparison of anti-lymphocyte immunotoxins containing different ribosome-inactivating proteins and antibodies", *Clin. Exp. Immunol.* 89, 341 (1992).

3. Biotherapeutic Agents

The biotherapeutic agents of the present invention can generally be defined as compounds formed by linking cytotoxic agents, such as the toxins disclosed above, to carriers capable of delivering the cytotoxic agents to specific target cells or organs. Thus, the biotherapeutic agents of the present invention can include not only immunotoxin as defined above, but also, constructs synthesized by known methods of genetic engineering, e.g., recombinant proteins. The activity of these biotherapeutic agents depends not only on the toxin utilized, but also on efficient binding of antibody to antigen, endocytosis, and intracellular release of functional ribosome inactivating proteins. For example, TP-3-PAP is a biotherapeutic agent composed of monoclonal antibody TP-3, an $IgG_{2b}$ monoclonal antibody which recognizes mesenchymal tumors, covalently coupled to the ribosome inhibitory plant toxin PAP. Since the potency of PAP is such that a few molecules in the cytoplasm are sufficient to kill a cell, TP-3 antigen density may be less important than specificity of binding in determining ultimate usefulness and therapeutic index of this particular immunotoxin. Vitetta et al., "Immunotoxins" In: *Biologic Therapy of Cancer*, V. T. DeVita, Jr., S. Hellman, S. A. Rosenberg (eds.), J. B. Lippincott Company, pp. 482–495 (1991). Furthermore, the unexpected potency of TP-3-PAP, which seems unique to this PAP immunotoxin, allows the administration of less immunotoxin to achieve a therapeutic benefit.

4. Production and Purification of Biotherapeutic Agents

Preferred biotherapeutic agents are formed by linking an effective cytotoxic amount of PAP molecules to each molecule of TP-1 or TP-3. For example, a reagent useful in the practice of the invention is a mixture of TP-3-PAP having 1-3 PAP molecules per TP-3 molecule.

Heterobifunctional cross-linking reagents useful in the formation of monoclonal antibody-PAP immunotoxins include SPDP (N-succinimidyl 3-(2-pyridyldithio) propionate) and its derivatives. For example, the particular TP-3-PAP employed in the examples hereinbelow is prepared by modifying TP-3 MoAb with the crosslinking agent SPDP and then reacting the modified TP-3 with a 3.5:1 molar excess of 2-iminothilane modified PAP.

5. Modes of Administration of the Biotherapeutic Agents

The biotherapeutic agents of the present invention can be formulated as pharmaceutical compositions and administered to a mammalian host, such as a human patient, in a variety of forms adapted to the chosen parenteral route of administration, i.e., by intravenous, intramuscular or subcutaneous routes.

a. Dosage Forms

It is preferred that the biotherapeutic agents of the present invention be parenterally administered, i.e., intravenously, or subcutaneously by infusion or injection. Solutions or suspensions of the biotherapeutic agent can be prepared in water, or isotonic saline, such as PBS, optionally mixed with a nontoxic surfactant. Dispersions can also be prepared in glycerol, liquid polyethylene glycols, DMA, vegetable oils, triacetin, and mixtures thereof. Under ordinary conditions of storage and use, these preparations may contain a preservative to prevent the growth of microorganisms. Because sarcomas often metastasize to the lungs, more specific delivery of the therapeutic agent to the lungs may be accomplished via aerosol delivery systems. The pharmaceutical dosage form suitable for aerosol delivery can include adipot formulations such as a liposome of suitable size.

The pharmaceutical dosage form suitable for injection or infusion use can include sterile aqueous solutions or dispersions or sterile powders comprising the active ingredient which are adapted for the extemporaneous preparation of sterile injectable or infusible solutions or dispersions. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, and liquid polyethylene glycols, and the like), vegetable oils, nontoxic glyceryl esters, lipids (for example, dimyristoyl phosphatidyl choline) and suitable mixtures thereof. The proper fluidity can be maintained, for example, by the formation of liposomes, by the maintenance of the required particle size in the case of dispersion or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers or sodium chloride. Prolonged absorption of the injectable compositions can be brought about by the inclusion in the compositions of agents delaying absorption, for example, aluminum monostearate hydrogels and gelatin.

Sterile injectable or infusable solutions are prepared by incorporating the biotherapeutic agents in the required amount in the appropriate solvent with various of the other ingredients enumerated above, and as required, followed by filter sterilization. In the case of sterile powders for the preparation of sterile injectable or infusable solutions, the preferred methods of preparation are vacuum drying and the freeze drying techniques, which yield a powder of the active ingredient plus any additional desired ingredient present in the previously sterile-filtered solutions.

b. Dosages

The dosage of the biotherapeutic agents in said composition can be varied widely, in accord with the size, age and condition of the patient and the target cancer. Based on animal data, it is expected that the dosage can be varied between 0.025 mg/kg and 1 mg/kg, administered over a period of about 1 to 7 days.

The invention will be further described by reference to the following detailed examples, wherein the OHS line is an adherent human osteosarcoma line with high constitutive expression of the TP1/3 antigen. OHS was derived by Fostad et al. from an adolescent with metastatic osteosarcoma which occurred 13 years after retinoblastoma. ("Characteristics of a cell line established from a patient with multiple osteosarcoma, appearing 13 years after treatment for bilateral retinoblastoma", Int. J. Cancer, 38, 33 (1986)). For the present studies OHS was obtained from Dr. Deborah Haines (Western College of Veterinary Medicine, Saskatoon, Canada) and passaged in RPMI 1640 with 2 mM L-glutamine, 100 U/ml penicillin, 100 mcg/ml streptomycin and 10% FCS. D17 (canine osteosarcoma) was obtained from Dr. Stuart Helfand (University of Wisconsin, Madison Wis.); D17 is negative for TP-3 antigen. The human CD19+ ALL cell line, RS4;11, was obtained from Dr. John Kersey (University of Minnesota, Minneapolis Minn.) and used as a negative control line for TP-3-PAP studies.

EXAMPLE 1

TP-3 MoAb Production and Purification

The TP-3 MoAb hybridoma was obtained by immunization of BALB/c mice against a human osteosarcoma xenograft as described by Fostad et al. ("Characteristics of a cell line established from a patient with multiple osteosarcoma, appearing 13 years after treatment for bilateral retinoblastoma", Int. J. Cancer, 38, 33 (1986)). Briefly, TP-3 hybridoma cells were cultured in DMEM (Celox, Hopkins Minn.) containing 25 mM HEPES, 2 mM L-glutamine, 100 U/ml penicillin, 100 µg/ml streptomycin, 10 mM nonessential amino acids, 100 mM sodium pyruvate, and 10% fetal calf serum (FCS; Sigma, St. Louis Mo.). BALB/c mice were primed with 0.5 ml pristane (Aldrich Chemical Co., Milwaukee Wis.) intraperitoneally (i.p.) 7 days before injection of $2 \times 10^6$ TP-3 hybridoma cells i.p. Ascites containing TP-3 MoAb was collected, centrifuged at 12,000g×20 minutes, pooled, and filtered through a 0.22 µm filter. TP-3 MoAb was further purified using ammonium sulfate precipitation and affinity chromatography with protein A agarose (Immunopure Plus immobilized protein A; Pierce, Rockford Ill.). Elution from Protein A was accomplished with Immunopure elution buffer (Pierce). TP-3 was dialyzed against PBS and sterile filtered prior to use.

EXAMPLE 2

TP-3-PAP Immunotoxin Synthesis

TP-3 MoAb was purified as described in Example 1, above, while PAP was purified using spring leaves of pokeweed (*Phytolacca americana*) as starting material as previously described by Irvin et al. ("Pokeweed antiviral protein: ribosome inactivation and therapeutic applications", *Pharmac. Ther.*, 55, 279 (1992)).

Purified TP-3 MoAb at a concentration of 8 mg/mL in PBS, was reacted with a 3.5:1 molar excess of SPDP (N-succinimidyl 3-(2-pyridyldithio)propionate (Pharmacia, Biotech Inc., Piscataway, N.J.) which was freshly prepared in DMSO and diluted 1:10 in PBS immediately prior to use. PAP, purified and dialyzed against PBS, pH 8.0, was concentrated to 10 mg/mL and mixed with a 3.5:1 molar excess of 2-iminothiolane HCl (Pierce, Rockford, Ill.) which was prepared just prior to use in 50 mM sodium phosphate, pH 8.6. Both modification procedures were carried out for 1.5 hours at room temperature with gentle rocking in sterile and pyrogen-free glass vials.

Excess cross linking agents were removed by passage through prepacked Sephadex G-25 PD-10 columns (Pharmacia, Biotech Inc., Piscataway, N.J.) equilibrated in PBS. Fractions were monitored at 280 nm and those containing the majority of the protein were combined and the total amounts of MoAb and PAP were determined using $E_{280nm}$ (1%) values of 1.43 and 0.83 for MoAb and PAP, respectively. Thiolated PAP was added to the SPDP-modified MoAb at a final molar ratio of 3.5:1, PAP:MoAb. The mixture was gently rocked for 3 hours at room temperature, incubated overnight at 4° C., and rocked at room temperature for another 3 hours before being filtered in preparation of the HPLC purification step.

Figure 1A:
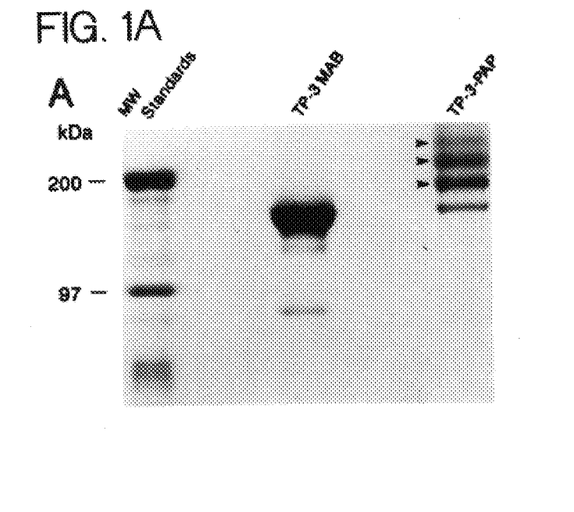
FIG. 1A is an HPLC elution profile which shows TP-3-PAP eluting at 38 min and free PAP eluting at 56 min.

Gel filtration chromatography to remove unreacted PAP and high molecular weight ($\geq$300 kd) immunoconjugates/aggregates was carried out using a 21.5×600 mm Spherogel TSK3000SW HPLC column (Beckman Instruments and TosoHaas) equilibrated at a flow rate of 3 mL/min in 100 mM sodium phosphate, pH 6.8. Unconjugated TP-3 MoAb was removed from the HPLC-purified TP-3-PAP immunotoxin preparation using ion-exchange chromatography. The HPLC fractions were concentrated and dialyzed overnight at 4° C. against 10 mM sodium phosphate pH 7.1. The pH and conductivity of the dialyzed TP-3-PAP were adjusted to that of the CM-Sepharose resin, which was first equilibrated in 10 mM sodium phosphate pH 6.5. The CM-Sepharose column was washed briefly with 10 mM sodium phosphate pH 7.1; TP-3 MoAb was eluted in 10 mM sodium phosphate, pH 7.8, containing 20 mM sodium chloride, and TP-3-PAP immunotoxin was recovered from the PBS, pH 7.5, eluant. As shown in FIG. 1, TP-3-PAP immunotoxin began to elute approximately 34 minutes after injection, followed closely by unreacted TP-3 MoAb. Free PAP eluted at 56 min and was well-separated from the immunotoxin. The HPLC semi-purified material still contained significant amounts of unreacted TP-3 MoAb.

Figure 1B:
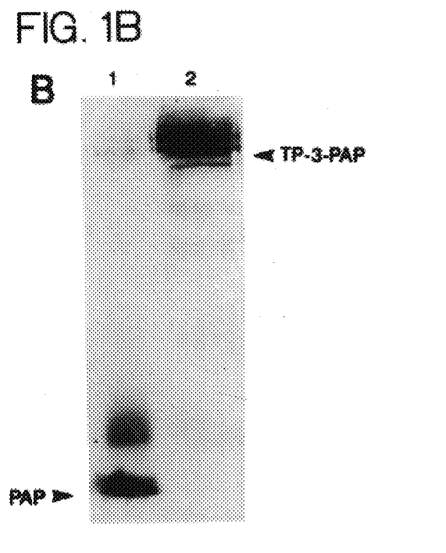
FIG. 1B is a Coomassie Blue stained gel of TP-3 and TP-3-PAP and FIG. 1C is a Western Blot conducted with anti-PAP.

The purification procedures were monitored by SDS-PAGE using 5% separating gels. SDS-PAGE scanning of the dried gel revealed <5% PAP in the final TP-3-PAP immunotoxin preparation which also contained 14% MoAb (150 kd), 34 % of the 180 kd species consisting of one PAP molecule disulfide-linked to one MoAb molecule, 34% of the 210 kd species consisting of two PAP molecules linked to one MoAb molecule, and 18% of the 240 kd species consisting of three PAP molecules linked to each MoAb molecule (FIG. 1). Coomassie Blue stained gels were dried and scanned using a Beckman DU62 spectrophotometer and GelScan Soft-Pac Module software. Protein concentrations were measured using the Bicinchoninic acid assay system (Sigma). In addition, a silver stain kit obtained from Bio-Rad Laboratories was used to visualize the protein bands after SDS-PAGE with greater sensitivity of detection.

Figure 1C:
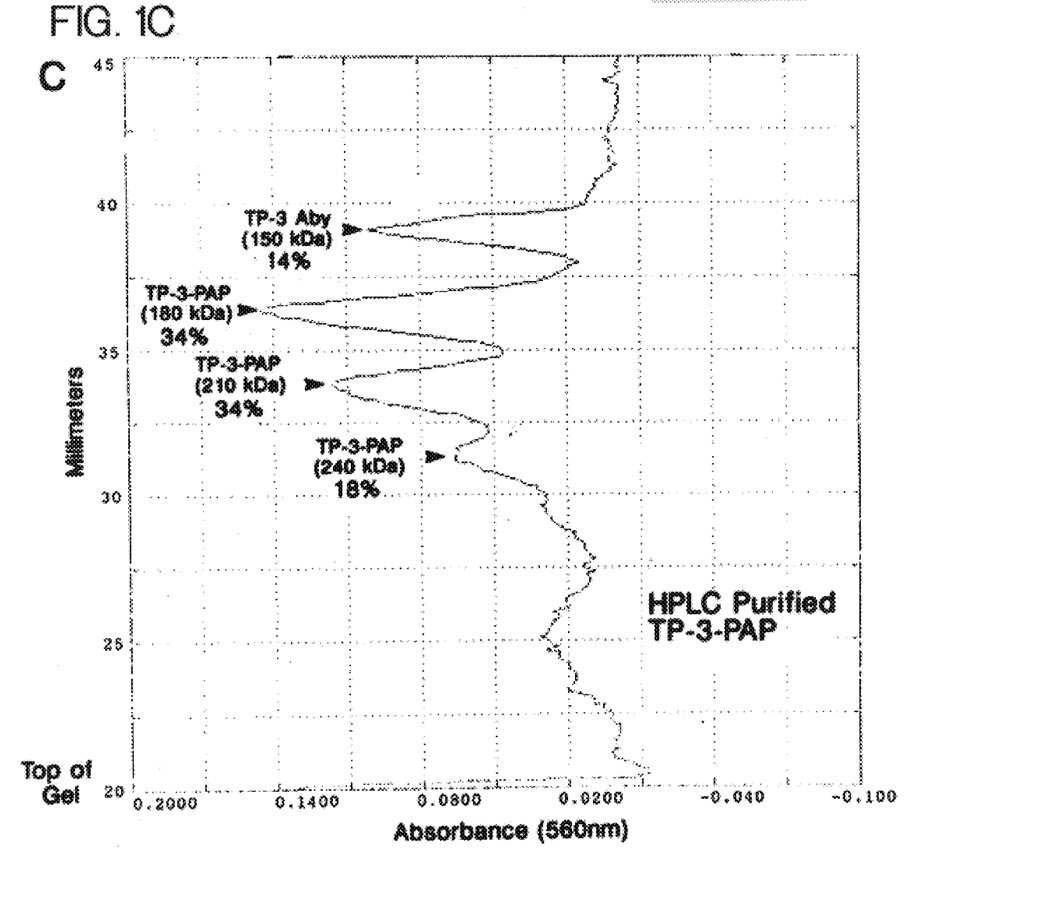

The presence of TP-3 monoclonal antibody and PAP moieties in the TP-3-PAP immunotoxin, as well as the absence significant free PAP contamination in the purified TP-3-PAP immunotoxin was confirmed using Western blot analysis (FIG. 1C) and a detection kit obtained from Bio-Rad Laboratories, as previously described by Myers et al., cited supra. The anti-PAP primary antibody was generated in rabbits that had been hyperimmunized with highly purified PAP. Immunoblotting was also done using alkaline phosphatase-conjugated goat anti-mouse IgG (Sigma Chemical Co., St. Louis, Mo.) to detect unconjugated anti-TP-3 monoclonal antibody remaining in the purified immunoconjugate preparations, as previously reported by Myers et al., cited supra. Protein concentrations were determined using the Bicinchoninic Assay System obtained from Sigma.

EXAMPLE 3

TP-3-PAP Immunotoxin Activity Against Human OHS Osteosarcoma Cells

Solutions of MoAb, toxins, and immunotoxins were tested for effects on OHS cell growth using a standard $^3$H thymidine incorporation assay.

After incubation of samples and indicator OHS cells for 2–4 days, 25 μl (2 μCi)) of $^3$H thymidine (Dupont NEN, Boston Mass.) was added to each well and plates incubated for 6 hours prior to harvesting DNA onto filter paper discs with a PHD cell harvesting apparatus (Cambridge Technology, Inc., Watertown Mass.). After addition of liquid scintillation fluid (Cytoscint; ICN, Costa Mesa Calif.), radioactivity was determined using an LKB 1216 liquid scintillation counter. Data was analyzed using an Excel macro routine written by Dr. Bob Jarvis (University of Minnesota Computer Sciences) to determine the mean and standard deviation of each triplicate set of samples. Clonogenic assays were done with OHS using methods previously reported by Uckun et al. ("Use of a novel colony assay to evaluate the cytotoxicity of an immunotoxin containing pokeweed antiviral protein against blast progenitor cells freshly obtained from patients with common B-lineage acute lymphoblastic leukemia", *J. Exp. Med.* 163 347 (1986)).

Figure 2A:
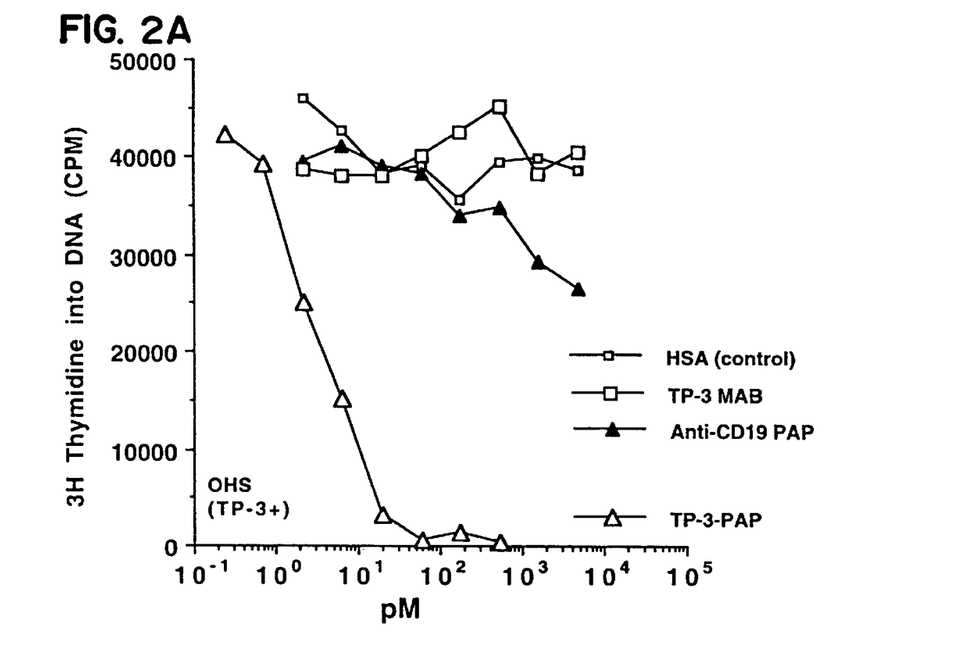

TP-3-PAP immunotoxin was found to effectively kill TP-3+ OHS sarcoma cells. For example, FIG. 2 shows the effect of TP-3 MoAb, TP-3-PAP, PAP alone, and an irrelevant immunotoxin construct which binds CD19 on B cells (B43-PAP), on proliferation of human OHS osteosarcoma cells. The TP-3 MoAb alone (i.e. without PAP toxin) had no effect on proliferation; cells incorporated $^3$H thymidine into DNA in a manner identical to media with human serum albumin (HSA; FIG. 2A). TP-3-PAP, however completely eliminated uptake of $^3$H thymidine in the first 4 wells which had OHS cells; OHS did not survive immunotoxin treatment until TP-3-PAP was diluted to 20 pM or less. Furthermore, different lots of TP-3-PAP yielded reproducible and highly efficient killing of OHS. $^3$H thymidine proliferation assays using OHS in 5 separate experiments with lot 1 of TP-3-PAP yielded a mean $IC_{50}$ value of 3.1±1.0 pM. Three different experiments using a second lot of TP-3-PAP yielded a mean $IC_{50}$ of 4.1±0.3 pM. The overall mean $IC_{50}$ was 3.5±1.0 pM.

Figure 2B:
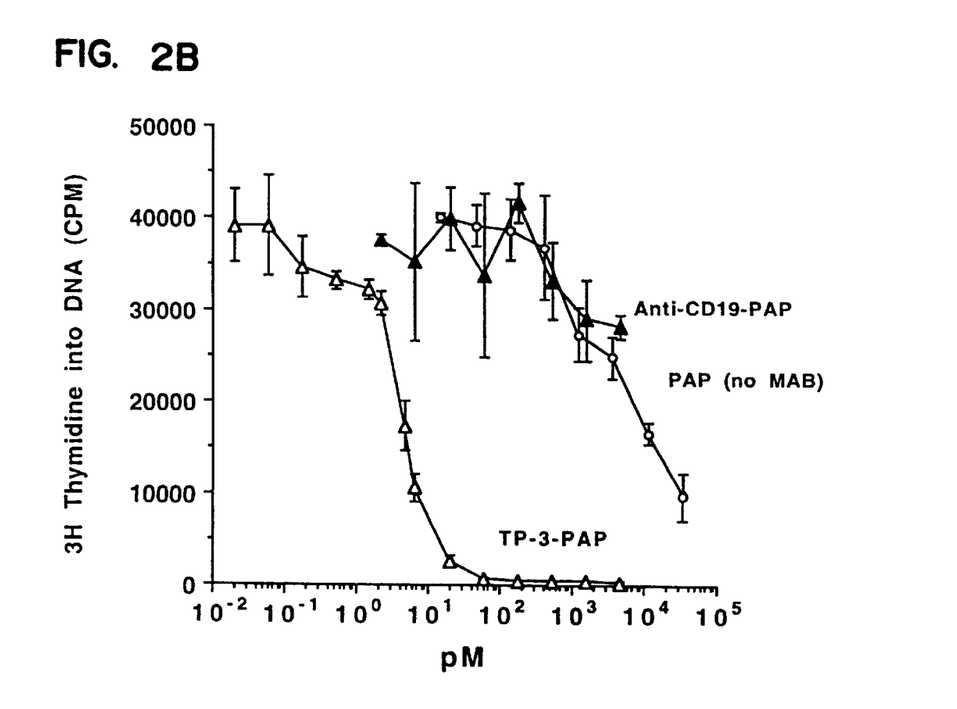
FIG. 2B shows that the TP-3 binding moiety was necessary for PAP toxin's effect on OHS cells at low concentrations. B43-PAP, an anti-CD19-PAP immunotoxin which does not bind CD19 negative OHS cells had minimal effects even at very high concentrations (>1000 pM).
Figure 3A:
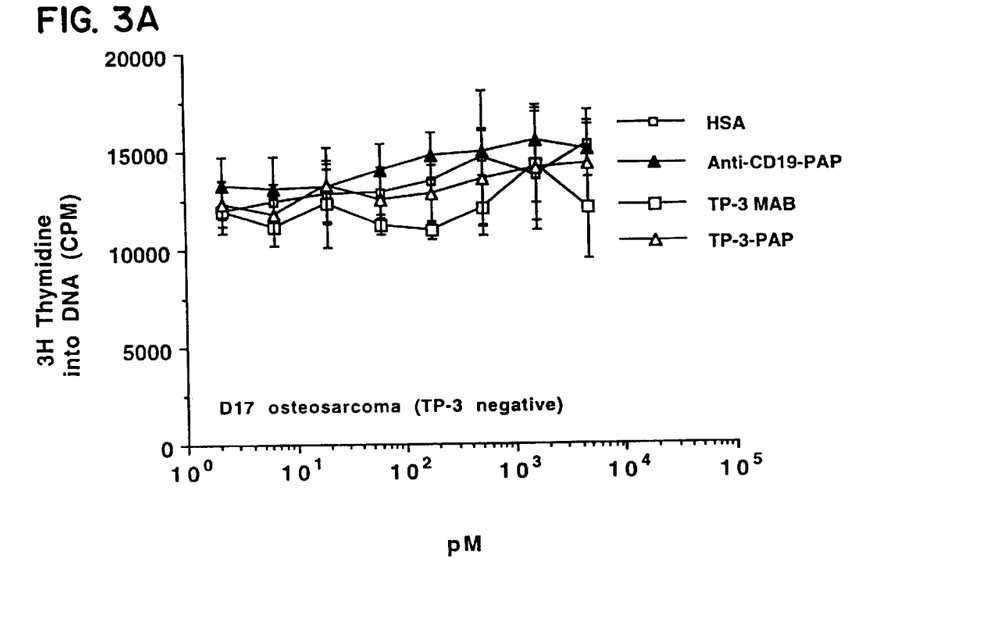
FIG. 3A shows the effect on a culture of canine D17 osteosarcoma of human serum albumin (HSA), TP-3 MoAb, TP-3-PAP immunotoxin or B43-PAP immunotoxin.
Figure 3B:
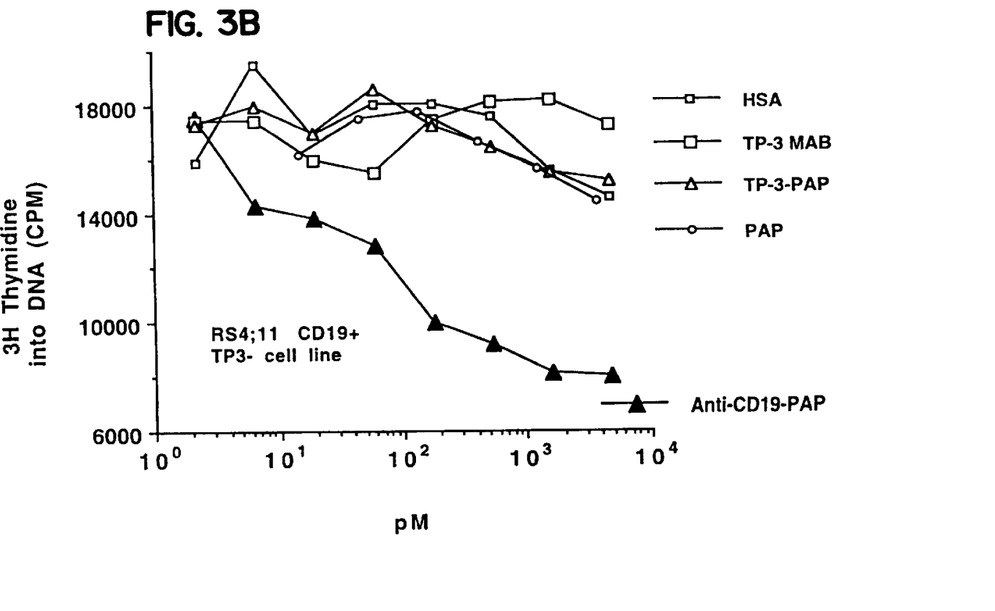
FIG. 3B illustrates the effect of HSA, TP-3 MoAb, TP-3-PAP and B43-PAP on the CD19+ RS4;11 human ALL cell line.

These results also illustrate that the killing of cells by TP-3-PAP is highly specific for cells expressing TP-3 antigen. PAP alone or B43-PAP, an anti-CD19 immunotoxin, had no effect on OHS proliferation until concentrations were 10,000 pM or more (see FIG. 2B). This represents a >3,000 fold increase in cytotoxicity if the TP-3 MoAb was conjugated to the PAP moiety. If tumors did not express the TP-3 antigen, killing by TP-3-PAP did not occur at concentrations <$10^4$ pM (FIGS. 3A and 3B). B43-PAP, however, was active against the CD19+ cell line RS4;11 (FIG. 3B). Thus, killing by the PAP immunoconjugates was conferred by specific MoAb binding.

A highly sensitive in vitro serial dilution clonogenic assay system was used to determine the log kill efficacy of TP-3-PAP immunotoxin against clonogenic OHS human osteosarcoma cells. As shown in Table 2 below, a 4 hour treatment with 100–3000 ng/mL TP-3-PAP at 37° C./5% $CO_2$ killed clonogenic OHS cells in a dose-dependent fashion with a maximum of 3.9±0.2 logs at 1000 ng/mL (5.6 nM). Notably, this 4-hour treatment protocol with TP-3-PAP concentrations≦100 ng/mL did not significantly inhibit the clonogenic growth of OHS cells (log kill≦0.2 log). By comparison, an 18 hours exposure to 1 ng/mL–3000 ng/mL TP-3-PAP killed clonogenic OHS cells in a dose-dependent fashion with 1.2 log kill at 100 ng/mL and >3.9 logs kill at concentrations ≧300 ng/mL (Table 2).

TABLE 2

Anti-tumor activity of TP-3-PAP against Clonogenic Osteosarcoma Cells
(OHS Human Osteosarcoma Clonogenic Assay)

| Incubation Time (hr) | TP-3-PAP Conc. (ng/ml) | Colony Units (mean ± SEM) | Log Kill (Mean ± SEM |
|---|---|---|---|
| 4 | 0 | 4588 ± 1556 | 0.00 ± 0.00 |
| 4 | 10 | 4588 ± 1556 | 0.00 ± 0.20 |
| 4 | 30 | 2683 ± 910 | 0.23 ± 0.20 |
| 4 | 100 | 2683 ± 910 | 0.23 ± 0.20 |
| 4 | 300 | 313 ± 135 | 1.16 ± 0.23 |
| 4 | 1000 | 4 ± 1 | 3.91 ± 0.23 |
| 4 | 3000 | 4 ± 1 | 3.91 ± 0.23 |
| 18 | 0 | 4588 ± 1556 | 0.00 ± 0.00 |
| 18 | 1 | 2052 ± 550 | 0.34 ± 0.22 |
| 18 | 10 | 917 ± 311 | 0.69 ± 0.20 |
| 18 | 30 | 313 ± 321 | 0.58 ± 0.18 |
| 18 | 100 | 120 ± 135 | 1.16 ± 0.23 |
| 18 | 300 | 62 ± 27 | 1.86 ± 0.23 |
| 18 | 1000 | 4 ± 1 | 3.91 ± 0.23 |
| 18 | 3000 | 4 ± 1 | 3.91 ± 0.23 |

EXAMPLE 4

In Vivo Administration of TP-3-PAP

Mice were fed and housed by University of Minnesota Research Animal Resources in accordance with NIH guidelines. Procedures and protocols involving live animals were approved by the University of Minnesota Animal Care Committee. The p80 antigen (TP-3 antigen) positive MCA106 soft tissue sarcoma was obtained from Dr. Jim Mule (NCI, Bethesda Md.) and serially passaged in female C57BL/6 mice. Tumors were harvested, minced, and digested by stirring on a magnetic stir plate for 4 hours using 0.4 mg/ml hyaluronidase, 0.05 mg/ml deoxyribonuclease, and 4.0 mg/ml collagenase (Sigma) in RPMI 1640 with 100 u/ml penicillin, 100 μcg/ml streptomycin, and 2 mM L-glutamine. Cells were filtered through Cell Strainers™ (Falcon, Becton Dickinson), washed three times in Hank's Balanced Salt Solution (HBSS) without $Ca^{2+}$, or $Mg^{2+}$, and concentration adjusted to 1×$10^5$ cells/ml. Pulmonary metastases were established by intravenous injection of MCA106 sarcoma cells (0.4 cc containing 40,000 cells/mouse) into the tail vein of 6–8 week old female C57BL/6 mice.

Groups of 10 mice with pulmonary metastases were treated with antibody alone or immunotoxin preparations i.p. Numbers of metastases were evaluated by direct counting 14 days after establishment of metastases. After asphyxiation with $CO_2$, India ink (5% with 3 gtt $NH_4OH$/100 ml) was injected into the trachea. Lungs and heart were removed en bloc and placed into Fekete's Solution (300 ml 70% ethanol, 30 ml 10% formalin, and 15 ml glacial acetic acid). Lungs were coded and counted by at least two blinded observers. Differences in number of metastases between treatment groups were evaluated using Student's unpaired t-test (InStat™, GraphPad Software, San Diego Calif.).

Figure 4:
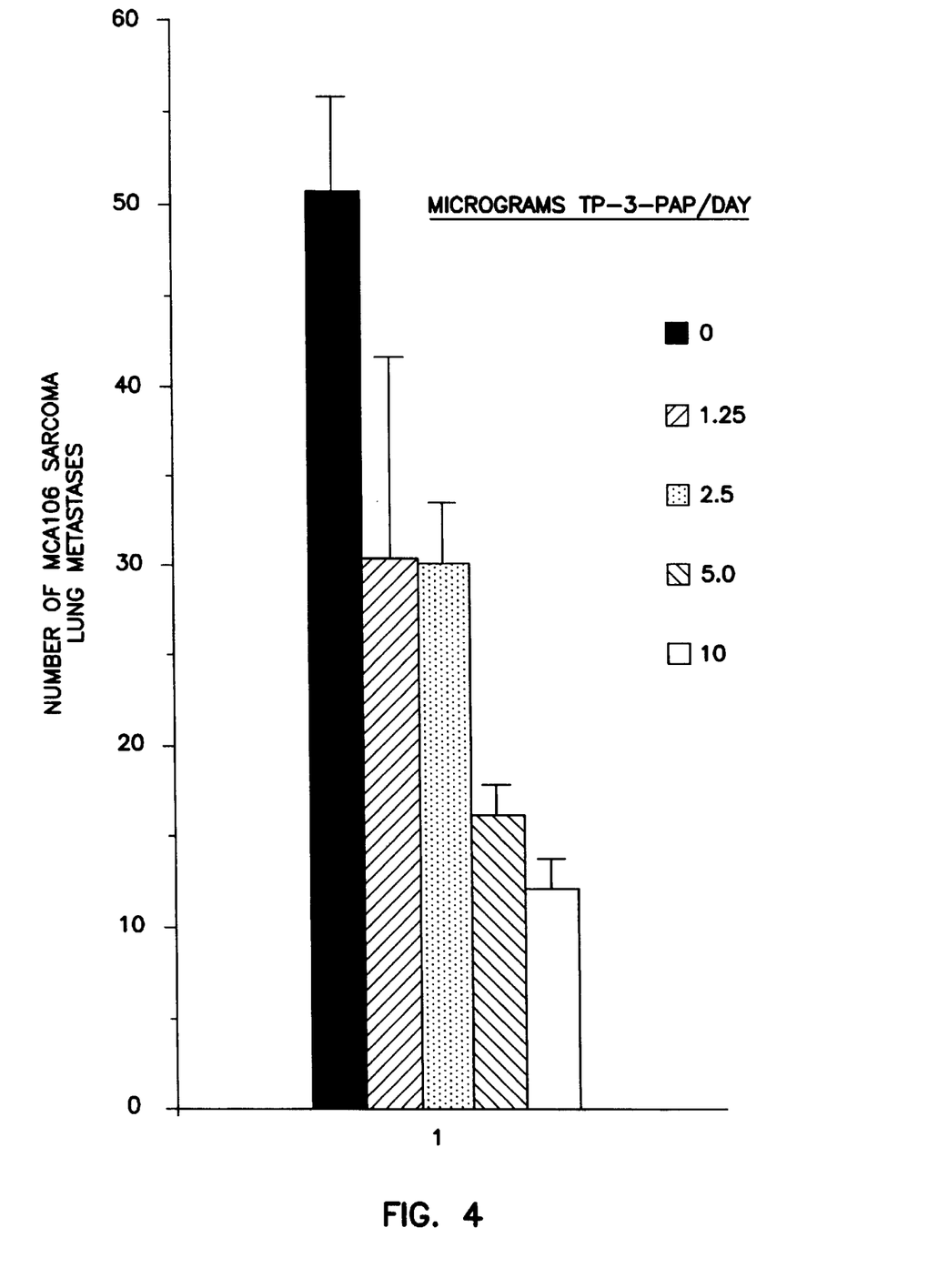
FIG. 4 is a bar graph that is illustrative of the dose response of TP-3-PAP immunotoxin against MCA106 sarcoma lung metastases.

TP-3-PAP was found to be active in vivo against lung metastases. Table 3, below, and FIG. 4 summarize results using TP-3-PAP in mice bearing MCA106 pulmonary metastases. Neither TP-3 MoAb alone nor irrelevant B43-PAP immunotoxin had any effect on numbers of lung metastases (Table 3). Three consecutive days of i.p. TP-3-PAP immunotoxin treatment, however, was able to significantly reduce numbers of pulmonary metastases (p<0.04). A dose response relationship was examined in a second experiment (FIG. 4). Reduction of pulmonary metastases by TP-3-PAP was dose related and highly significant at doses tested (Table 3). Interestingly, not only were significantly fewer numbers of metastases seen in TP-3-PAP treated mice, but the size of lung metastases in TP-3-PAP treated mice was much smaller than metastases in control mice. Cumulative doses of TP-3-PAP required for significant anti-tumor effects were between 3.75 µg and 30 gg/mouse (0.2 to 1.5 mg/kg).

TABLE 3

Reduction of Lung Metastases after TP-3-PAP but No Effect of Irrelevent Immunotoxin B43-PAP or TP-3 MAB alone

| Treatment[b] | Dose of Immunotoxin[c] | Number of Lung Metastases[a] | | Student's t-test p valued[d] |
|---|---|---|---|---|
| | | Mean | SEM | |
| HBSS (control) | none | 10.2 | 2.5 | — |
| TP-3 MAB | 0.0 | 16.4 | 2.8 | NS |
| TP-3-PAP | 1.1 | 5.2 | 1.7 | NS |
| TP-3-PAP | 3.3 | 2.2 | 4.2 | 0.047 |
| TP-3-PAP | 10.0 | 0.75 | 0.75 | 0.039 |
| B43-PAP | 10.0 | 6.5 | 2.8 | NS |

[a]metastases counted on day 14
[b]MCA 106 sarcoma has no CD19 epitopes recognized by B43-PAP immunotoxin; however MCA 106 tumor cross reacts with TP-3 MAB
[c]micrograms/day given on days 3, 4, 5
[d]compared to control group

EXAMPLE 5

TP-3-PAP Studies in a SCID Mouse Model of Human Osteosarcoma

Figure 5:
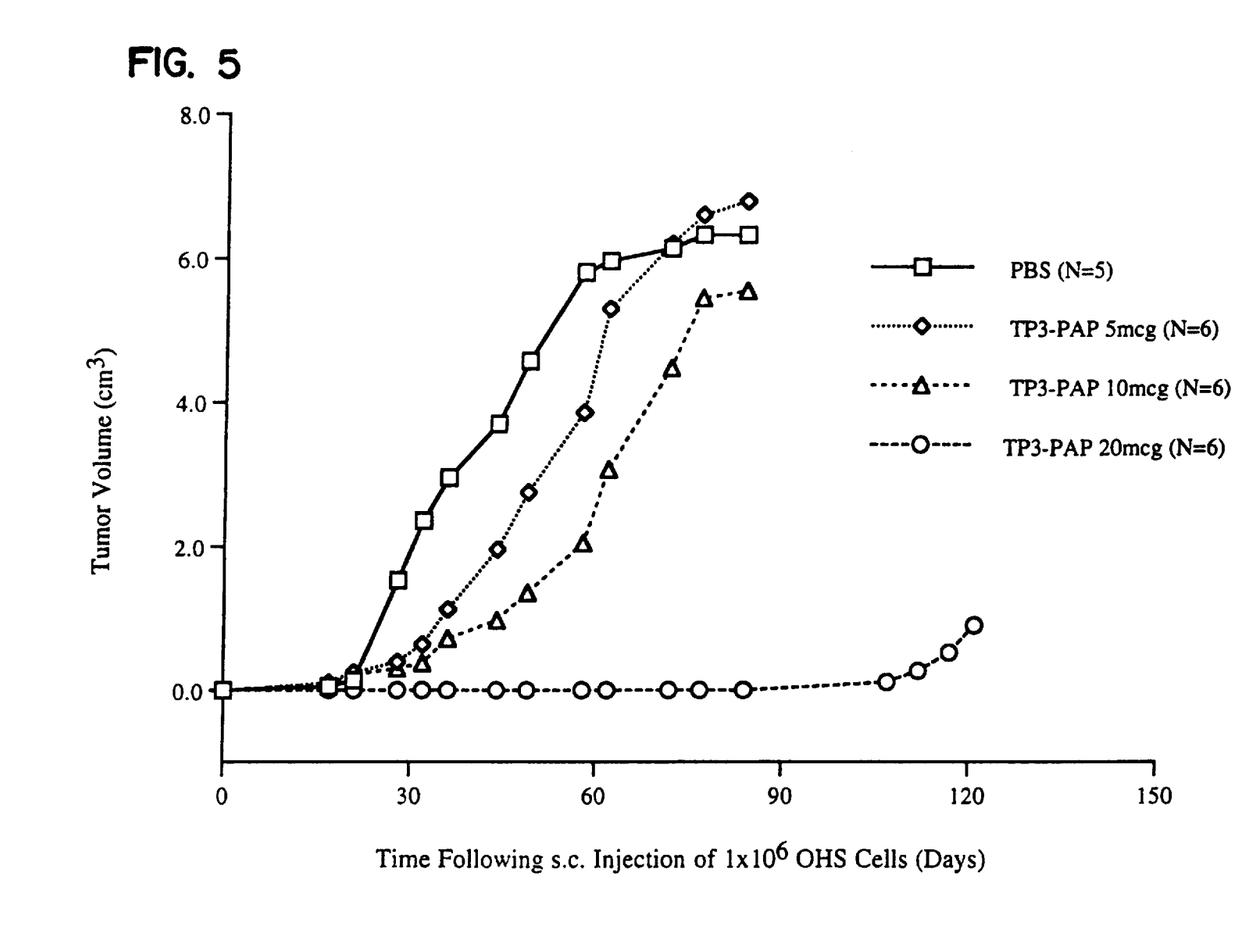
FIG. 5 depicts the effect of TP-3-PAP on the tumor volume of subcutaneous OHS (human osteosarcoma) after injection of the right hind limb of C.B.-17-SCID mice.

The in vivo anti-tumor efficacy of TP-3-PAP immunotoxin against human osteosarcoma in a SCID mouse xenograft model was investigated as follows. C.B-17-SCID mice were inoculated subcutaneously in their right hind leg with $1 \times 10^6$ OHS cells. Two hours following the s.c. tumor cell inoculation in the right hind leg, treatment with TP-3-PAP i.p. for three consecutive days was initiated. The majority of untreated mice developed OHS leg tumors by day 17 and by day 25 100% of untreated mice had leg tumors, with a mean volume of 137 $mm^3$. Tumor volumes are shown in FIG. 5.

Figure 6:
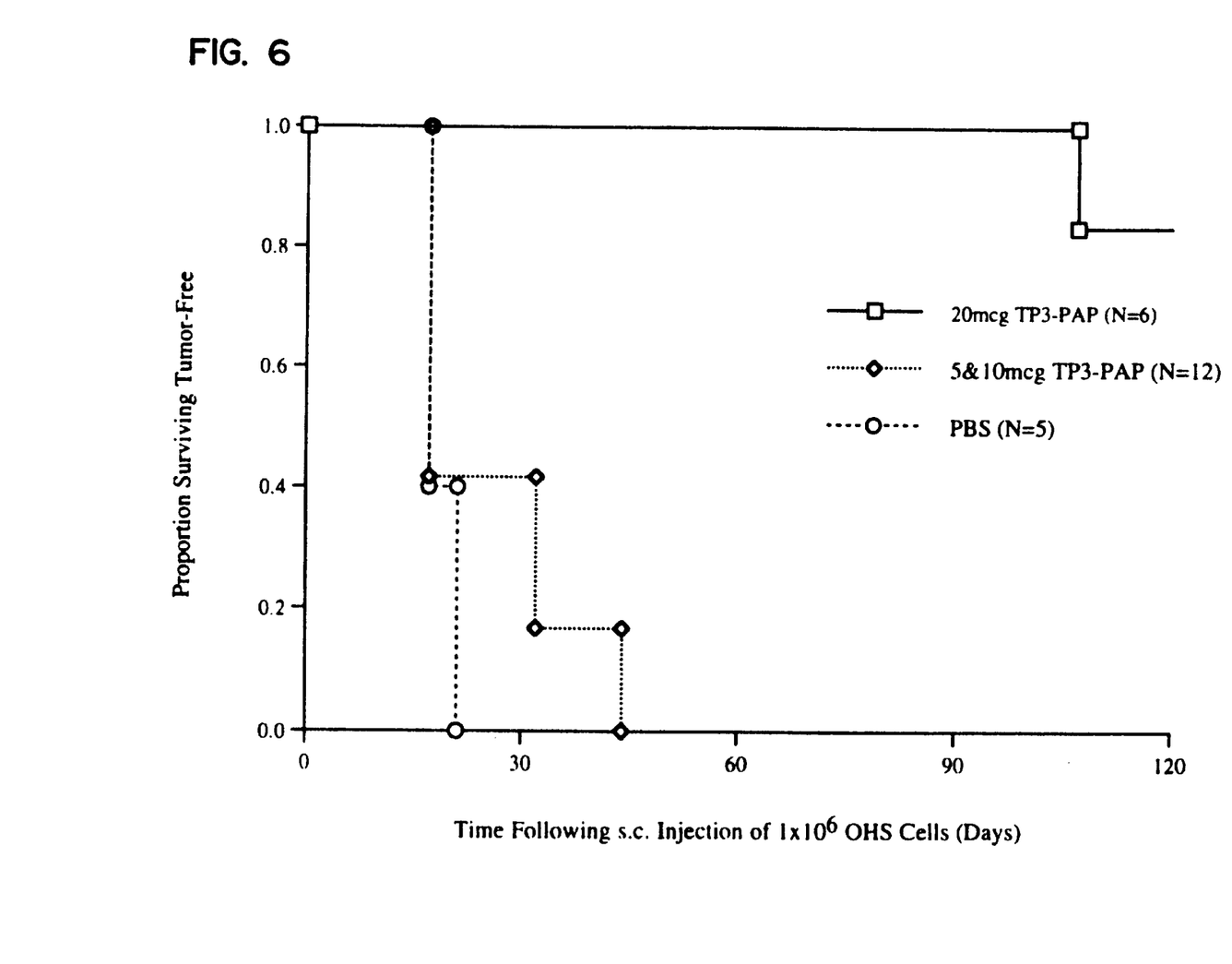
FIG. 6 illustrates the tumor free survival of mice injected with subcutaneous human osteosarcoma (OHS) and subsequently treated with either PBS or TP-3-PAP.

TP-3-PAP at dose levels 5, 10 or 20 µg/mouse significantly delayed the emergence and progression of OHS leg tumors in SCID mice. None of the SCID mice treated with 20 µg TP-3-PAP developed a leg tumor up to 110 days post inoculation. Most importantly, this was associated with improved survival. See FIG. 6. Furthermore, TP-3-PAP caused rapid necrosis of established large tumors. By contrast, a mixture of unconjugated TP-3 antibody, unconjugated PAP or B43-PAP (a control immunotoxin directed against leukemic cells), had no anti-tumor effect in this model system. These experiments establish that TP-3-PAP immunotoxin shows marked anti-tumor activity against human osteosarcoma xenografts in vivo and improves tumor-free interval of SCID mice challenged with an otherwise fatal number of human OHS osteosarcoma cells.

All publications, patents and patent documents are incorporated by reference herein, as though individually incorporated by reference. The invention has been described with reference to specific and preferred embodiments and techniques. However, it should be understood that many variations and modifications may be made while remaining within the spirit and scope of the invention.

What is claimed is:

1. A therapeutic method for the treatment of cancer comprising parenterally administering to a patient who is afflicted with a cancer expressing the p80 antigen a therapeutically effective amount of a biotherapeutic agent comprising an effective cytotoxic amount of pokeweed antiviral protein linked to an antibody or antigen-binding fragment thereof, which binds to the p80 osteosarcoma antigen.

2. The method of claim 1 wherein the cancer is a sarcoma.

3. The method of claim 2 wherein the sarcoma is an osteosarcoma.

4. The method of claim 1 wherein the biotherapeutic agent is administered in combination with a pharmaceutically acceptable liquid carrier.

5. The method of claim 4 wherein the liquid carrier comprises isotonic saline.

6. The method of claim 4 wherein the biotherapeutic agent is administered intravenously.

7. The method of claim 1 wherein the antibody if TP-1 (ATCC HB-12339), TP-3 (ATCC HB-12340), or an antigen-binding fragment thereof.

8. The method of claim 7 wherein the antibody is TP-3 or an antigen-binding fragment thereof.

9. The method of claim 8 wherein 1–3 molecules of PAP are linked to each molecule of PT-3 (ATCC HB-12340).

10. The method of claim 9 wherein the amount of the biotherapeutic agent is about 0.025 mg/kg to 1 mg/kg administered over about 1–7 days.

11. The method of claim 1 wherein the administration of the biotherapeutic agent is accompanied by the parenteral administration of an effective amount of an antieoplastic agent.

12. The method of claim 11 wherein the antineoplastic agent is chosen from the group consisting of doxorubicin, methotrexate, etoposide, an alkylating agent or a platinum compound.

13. The method of claim 12 wherein the antineoplastic agent is combined with a pharmaceutically acceptable carrier.

14. A therapeutic method for the treatment of cancer comprising parenterally administering to a patient who is afflicted with a cancer expressing the p80 antigen a therapeutically effective amount of a biotherapeutic agent comprising an effective cytotoxic amount of pokeweed antiviral protein linked to ATCC HB-12339.

15. A therapeutic method for the treatment of cancer comprising parenterally administering to a patient who is afflicted with a cancer expressing the p80 antigen a therapeutically effective amount of a hiotherapeutic agent comprising an effective cytotoxic amount of pokeweed antiviral protein linked to ATCC HB-12340.

16. A therapeutic method for the treatment of cancer comprising parenterally administering to a patient who is afflicted with a cancer expressing the p80 antigen a therapeutically effective amount of a biothcrapeutic agent comprising an effective cytotoxic amount of pokeweed antiviral protein linked to an anti-p80 antibody.

* * * * *